United States Patent
Rakow et al.

(10) Patent No.: US 7,906,223 B2
(45) Date of Patent: Mar. 15, 2011

(54) PERMEABLE NANOPARTICLE REFLECTOR

(75) Inventors: Neal A. Rakow, Woodbury, MN (US); Dora M. Paolucci, St. Paul, MN (US); Moses M. David, Woodbury, MN (US); Michael S. Wendland, North St. Paul, MN (US); John E. Trend, St. Paul, MN (US); Richard J. Poirier, White Bear Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1177 days.

(21) Appl. No.: 11/530,619

(22) Filed: Sep. 11, 2006

(65) Prior Publication Data

US 2008/0063874 A1   Mar. 13, 2008

(51) Int. Cl.
| | |
|---|---|
| B32B 19/00 | (2006.01) |
| B32B 27/32 | (2006.01) |
| B32B 9/04 | (2006.01) |
| B32B 13/04 | (2006.01) |
| B32B 9/06 | (2006.01) |
| B32B 15/04 | (2006.01) |
| G01N 21/00 | (2006.01) |
| G01N 31/22 | (2006.01) |
| G01J 1/48 | (2006.01) |
| B05D 3/02 | (2006.01) |

(52) U.S. Cl. ......... 428/689; 422/55; 422/58; 422/82.05; 422/82.09; 422/86; 427/372.2; 427/374.2; 427/383.1; 428/220; 428/446; 428/450

(58) Field of Classification Search .......... 422/55, 422/58, 82.05, 82.09, 86; 427/372.2, 374.2, 427/383.1; 428/220, 446, 450, 689
See application file for complete search history.

(56) References Cited

U.S. PATENT DOCUMENTS

| | | | |
|---|---|---|---|
| 3,971,373 | A | 7/1976 | Braun et al. |
| 4,153,661 | A | 5/1979 | Ree et al. |
| 4,208,194 | A | 6/1980 | Nelson |
| 4,778,987 | A | 10/1988 | Saaski et al. |
| 4,945,230 | A | 7/1990 | Saaski et al. |
| 4,948,639 | A | 8/1990 | Brooker et al. |
| 5,611,998 | A | 3/1997 | Aussenegg et al. |
| 5,659,296 | A * | 8/1997 | Debe et al. .............. 340/632 |

(Continued)

FOREIGN PATENT DOCUMENTS

EP   0677738 B1   4/1995

(Continued)

OTHER PUBLICATIONS

Machine English Translation of JP 2004-085872 provided by the JPO, retrieval date of Jun. 7, 2010.*

(Continued)

*Primary Examiner* — Jennifer C McNeil
*Assistant Examiner* — Jonathan C Langman
(74) *Attorney, Agent, or Firm* — Karl G. Hanson

(57) ABSTRACT

An optically-responsive multilayer reflective article is formed by applying a dilute solution or suspension of metallic nanoparticles to an optically-responsive detection layer. The solution or suspension is allowed to dry to form a semicontinuous liquid- or vapor-permeable light-reflective layer that will permit a liquid or vapor analyte to pass through the light-reflective layer to cause an optically-responsive change in the detection layer in the presence of the analyte.

39 Claims, 5 Drawing Sheets

U.S. PATENT DOCUMENTS

| | | | |
|---|---|---|---|
| 5,699,188 | A | 12/1997 | Gilbert et al. |
| 5,783,836 | A | 7/1998 | Liu et al. |
| 5,858,457 | A | 1/1999 | Brinker et al. |
| 5,882,774 | A | 3/1999 | Jonza et al. |
| 6,007,904 | A | 12/1999 | Schwotzer et al. |
| 6,010,751 | A | 1/2000 | Shaw et al. |
| 6,049,419 | A | 4/2000 | Wheatley et al. |
| 6,130,748 | A | 10/2000 | Krüger et al. |
| 6,312,793 | B1 | 11/2001 | Grill et al. |
| 6,573,305 | B1 | 6/2003 | Thunhorst et al. |
| 6,590,665 | B2 | 7/2003 | Painchaud et al. |
| 6,607,845 | B2 * | 8/2003 | Hirai et al. ............... 428/641 |
| 6,984,265 | B1 * | 1/2006 | Raguse et al. ............. 117/73 |
| 2004/0062682 | A1 | 4/2004 | Rakow et al. |
| 2004/0184948 | A1 | 9/2004 | Rakow et al. |
| 2006/0096911 | A1 | 5/2006 | Brey et al. |
| 2006/0197953 | A1 | 9/2006 | Perez et al. |

FOREIGN PATENT DOCUMENTS

| | | | |
|---|---|---|---|
| JP | 2004-085872 | * | 3/2004 |
| JP | 2004-335410 | | 11/2004 |
| WO | WO 97/01778 | | 1/1997 |
| WO | WO 98/48275 | | 10/1998 |
| WO | WO 2004/057314 A2 | | 7/2004 |
| WO | WO 2005/012397 A2 | | 2/2005 |
| WO | WO 2005/111588 A1 | | 11/2005 |
| WO | WO 2008/127350 A1 | | 10/2008 |

OTHER PUBLICATIONS

"Macromolecules", 2001, vol. 34, pp. 8792-8801.
"Science", 1999, vol. 283, p. 520.
Ogawa et al., *Chem. Commun.* pp. 1149-1150 (1996).
Kresge et al., *Nature*, vol. 359, pp. 710-712 (1992).
Jia et al., *Chemistry Letters*, vol. 33(2), pp. 202-203 (2004).
Wei et al, *Adv. Mater.*1998, vol. 10, p. 313 (1998).
"Polymers of intrinsic microporosity (PIMs): robust, solution-processable, organic microporous materials," Budd et al., *Chem. Commun.*, 2004, pp. 230-231.
Budd et al., *J. Mater. Chem.*, 2005, 15, pp. 1977-1986.
McKeown et al., *Chem. Eur. J.* 2005, 11, No. 9, 2610-2620.
V. A. Davankov and P. Tsyurupa, *Pure and Appl. Chem.*, vol. 61, pp. 1881-1889 (1989).
L. D. Belyakova, T. I. Schevchenko, V. A. Davankov and M.P. Tsyurupa, *Adv. in Colloid and Interface Sci.* vol. 25, pp. 249-266, (1986)).
Budd et al. in *Advanced Materials*, 2004, vol. 16, No. 5, pp. 456-459.
Product Data Sheet, "*Inkjet Silver conductor AG-IJ-G-100-S1*", Cabot Printable Electronics and Displays, Albuquerque, NM, pp. 1-2.
"Product Index" pp. 1-3 printed from Advanced Nano Products website http://www.anapro.com/english/product/product4_4.asp on Aug. 11, 2006, pp. 1-3.
Product Information Sheet, MS Series, "*No Clean and Lead-free Solder Paste*", downloaded from webpage: http://www.harima.co.jp/products/electronics/e_ms_series.html on Aug. 11, 2006, pp. 1-3.
Novacentrix™ Data Sheet, "*Metalon™ FS-066, Stretchable Nanosilver Ink*", 1 sheet.
Novacentrix™ Data Sheet, "*Metalon™JS-011, Nanosilver Ink-Aqueous dispersion*", 1 sheet.
Product Information Sheet, "Colloid", downloaded from webpage: http://www.npacorp.com/products/colloid.html on Aug. 11, 2006, 1 page.
Product Information Sheet, NovaCentrix, "*Metalon™ Brand Inks*", downloaded from webpage: http://www.nanoscale.com/products/ on Aug. 11, 2006, pp. 1-2.
Bauer et al., Maria, *Optimizing Novel Interference Film Sensor For Food Degradation*, NSTI-NANOTECH 2007, vol. 2, pp. 504-507 (Jan. 1, 2007).

* cited by examiner

PERMEABLE NANOPARTICLE REFLECTOR

This invention relates to reflective articles that include optically-responsive detection layers.

BACKGROUND

Various chemical, optical, or electronic detectors have been proposed for sensing the presence of gases, liquids, and other analytes. Optical detectors, for example, have been provided that employ a detection layer which is made from a material that modulates or otherwise alters transmitted or reflected light in the presence of an analyte. Reflective layers have been placed adjacent to the detection layer to guide light into or out of the detection layer. When an analyte is present, the detection layer undergoes a responsive change in an optical property. Reflective layers may also provide an indication that the analyte is present (e.g., via optical interference). For example, a calorimetric change may be provided in the presence of a vapor of interest by using a thin-film multilayer indicator having a porous detection layer whose optical thickness changes in the presence of the vapor, located between reflective and semireflective layers at least one of which is permeable to the vapor of interest. One such indicator employs a porous detection layer located between a reflective layer and a vapor-permeable semireflective layer and is described in U.S. Patent Application Publication Nos. US 2004/0062682 A1 (Rakow et al. '682) and US 2004/0184948 A1 (Rakow et al. '948).

SUMMARY OF THE INVENTION

Another such indicator employs a porous detection layer located between a semireflective layer and a vapor-permeable reflective layer proximate sorbent media and is described in copending U.S. patent application Ser. No. 11/530,614 filed even date herewith and entitled ORGANIC VAPOR SORBENT PROTECTIVE DEVICE WITH THIN-FILM INDICATOR. Both such indicators employ a light-reflective vapor-permeable surface adjacent a porous optically-responsive detection layer. The light-reflective surfaces in such indicators may be prepared for example via the initial deposition of a dense mirror using traditional metallization techniques (e.g., sputtering, evaporative deposition, electroplating or other electrochemical deposition) followed by a subsequent perforation step (e.g., etching or laser ablation) to provide pathways for vapor permeation into the detection layer pores. This approach, however, requires several exacting steps and specialized equipment. In addition, the deposition or perforation procedures may adversely affect the optical response of the detection layer or may adversely affect other layers within the indicator structure.

The present invention provides, in one aspect, a method for forming an optically-responsive multilayer reflective article. The method is relatively simple to perform, and may be accomplished by applying a dilute solution or suspension of metallic nanoparticles to an optically-responsive detection layer and allowing the solution or suspension to dry to form a semicontinuous liquid- or vapor-permeable light-reflective layer that will permit a liquid or vapor analyte to pass through the light-reflective layer to cause an optically-responsive change in the detection layer in the presence of the analyte. The light-reflective layer may have somewhat lower reflectivity than a typical metallized mirror made using traditional deposition techniques. However, the disclosed method enables deposition of a liquid- or vapor-permeable light-reflective layer without requiring specialized deposition equipment. The disclosed method is especially useful for forming a vapor-permeable light-reflective layer atop a porous detection layer.

The invention provides in another aspect an optically-responsive multilayer reflective article that comprises an optically-responsive detection layer in fluid communication with a semicontinuous liquid- or vapor-permeable light-reflective metal nanoparticle layer that will permit a liquid or vapor analyte to pass through the light-reflective layer and cause an optically-responsive change in the detection layer in the presence of the analyte.

These and other aspects of the invention will be apparent from the detailed description below. In no event, however, should the above summaries be construed as limitations on the claimed subject matter, which subject matter is defined solely by the attached claims, as may be amended during prosecution.

DETAILED DESCRIPTION

Figure 1:
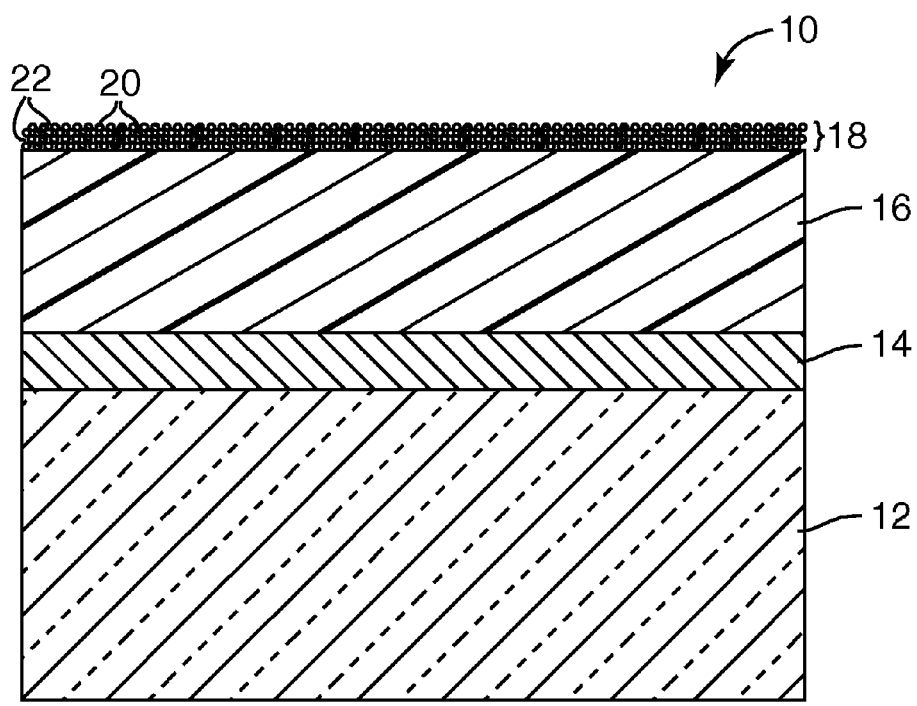
FIG. 1 is a schematic sectional view of a thin-film multilayer indicator that has a semicontinuous vapor-permeable semireflective metal nanoparticle layer in accordance with the present invention.

The terms set forth below are defined as follows:

"Liquid or vapor of interest" means an organic or inorganic liquid or vapor whose detection is desired, e.g., in ambient air or in a process atmosphere.

"Analyte" means the specific liquid or vapor of interest that is being detected, e.g., in a chemical or biochemical analysis.

"Optically-responsive" when used with respect to an article or a detection layer means that the article or detection layer exhibits a responsive change in a detectable optical property when an analyte is present, such as a change in optical thickness (viz., physical thickness or refractive index), reflectivity, phase shift, polarization, birefringence or light transmission.

"Reflective" when used with respect to a layer means that the layer reflects visible light.

"Semireflective layer" means a first reflective layer, which in reference to a second reflective layer, has lower reflectivity and greater light transmission than the second reflective layer and which may, for example, be used in spaced relation to the second reflective layer to provide interference coloration.

"Vapor-permeable" when used with respect to a reflective layer one side of which is in fluid communication with a detection layer means that if the other side of the reflective layer is exposed to an air stream containing 1000 ppm styrene monomer vapor flowing at 20 liters/min for 15 minutes, sufficient styrene monomer will pass through the reflective layer so that an optically-responsive change takes place in the detection layer.

"Liquid-permeable" when used with respect to a reflective layer one side of which is in fluid communication with a detection layer means that if the other side of the reflective layer is exposed to a solution containing 10% by volume acetone in water for 10 minutes, sufficient acetone will pass through the reflective layer so that an optically-responsive change takes place in the detection layer.

"Porous" when used with respect to a material means that the material contains a connected network of pores (which may, for example, be openings, interstitial spaces or other channels) throughout its volume.

"Size" when used with respect to a pore means the pore diameter for a pore having a circular cross section, or the length of the longest cross-sectional chord that may be constructed across a pore having a non-circular cross-section.

"Microporous" when used with respect to a material means that the material is porous with an average pore size of about 0.3 to 100 nanometers.

"Continuous" when used with respect to a layer of a material means that the layer is non-porous and is not vapor-permeable.

"Semicontinuous" when used with respect to a layer of a material means that the layer is porous and liquid- or vapor-permeable. A semicontinuous layer may be vapor-permeable but not liquid-permeable.

"Discontinuous" when used with respect to a layer of a material means that the layer has at least two separate and distinct islands of the material within a given plane with empty space therebetween, or at least two separate and distinct empty spaces (lakes) within a given plane with the material therebetween, and that the layer is vapor-permeable.

"Nanoparticles" means particles having an average particle diameter of about 1 to about 100 nm.

The disclosed optically-responsive multilayer articles may be used to detect a variety of liquids or vapors of interest. Representative liquids of interest include water, bodily fluids, oils, solvents, and other organic liquids. Representative vapors of interest include water vapor, gases, and volatile organic chemical compounds. Representative organic liquids and volatile organic chemical compounds include substituted or unsubstituted carbon compounds including alkanes, cycloalkanes, aromatic compounds, alcohols, ethers, esters, ketones, halocarbons, amines, organic acids, cyanates, nitrates, and nitriles, for example n-octane, cyclohexane, methyl ethyl ketone, acetone, ethyl acetate, carbon disulfide, carbon tetrachloride, benzene, styrene, toluene, xylenes, methyl chloroform, tetrahydrofuran, methanol, ethanol, isopropyl alcohol, n-butyl alcohol, t-butyl alcohol, 2-ethoxyethanol, acetic acid, 2-aminopyridine, ethylene glycol monomethyl ether, toluene-2,4-diisocyanate, nitromethane, and acetonitrile.

Referring to FIG. 1, optically-responsive multilayer article 10 provides a thin-film multilayer indicator that can detect the presence of a variety of analytes. Article 10 includes a substrate 12, continuous reflective layer 14, optically-responsive detection layer 16 and semicontinuous semireflective layer 18. Layer 14 may be formed using a variety of deposition techniques, including sputtering, evaporative deposition, electroplating or other electrochemical deposition, lamination or applying a suitably thick layer of a metallic paint. Layer 18 contains metal nanoparticles 20 arranged in a morphology which approximates a stack of cannonballs or marbles and through which liquid or vapor can permeate to reach detection layer 16, and is formed as described in more detail below. An analyte in the form of a liquid or vapor of interest near (e.g., above) layer 18 can pass through pores 22 into detection layer 16. Detection layer 16 can be formed in a variety of ways and is made from a suitable material or made with a suitable structure so that the layer's optical thickness changes (e.g., increases) upon exposure to the analyte. The resulting optical thickness change brings about a visibly perceptible appearance change in article 10. The change can be observed by looking at article 10 through semireflective layer 18. Ambient light represented by ray 24 passing through semireflective layer 18 and detection layer 16 is reflected by reflective layer 14 back through detection layer 16 and semireflective layer 18. If an appropriate initial or changed thickness has been chosen for detection layer 16, and provided that layers 14 and 18 are sufficiently flat, then interference coloration will be created or destroyed within device 10 and a visibly discernible change in the appearance of device 10 will be apparent when viewed through semireflective layer 18. Thus external equipment such as a powered light source, optical detector or spectral analysis would not be required to evaluate the condition of device 10, although such external equipment may be used if desired.

Figure 2:
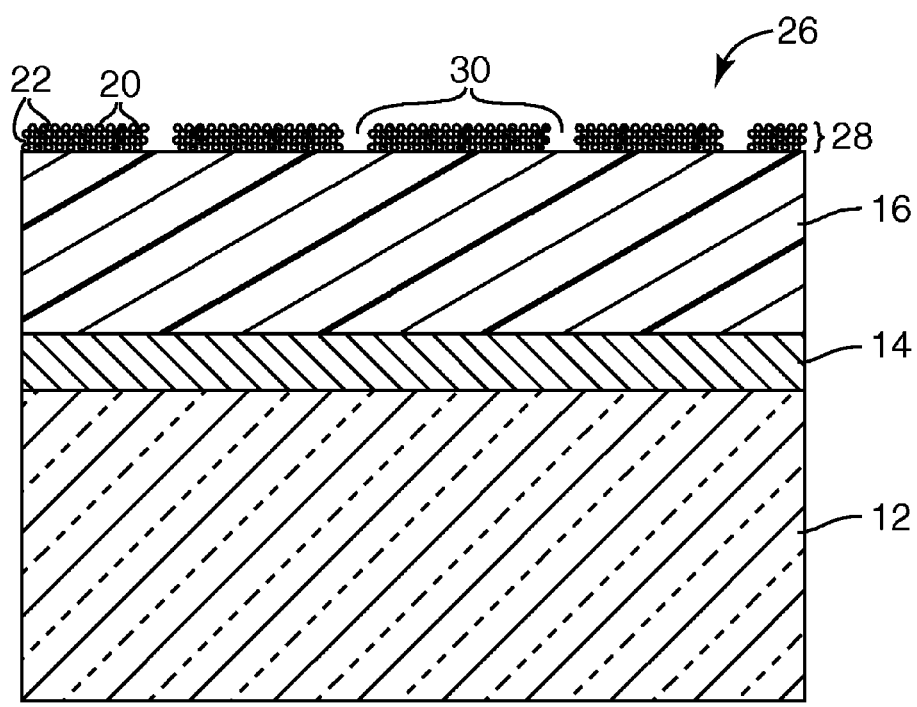
FIG. 2 is a schematic sectional view of a thin-film multilayer indicator that has a discontinuous vapor-permeable semireflective metal nanoparticle layer in accordance with the present invention.

FIG. 2 shows a schematic sectional view of an optically-responsive multilayer article 26 like article 10 in FIG. 1, but in which the metal nanoparticles 20 in layer 28 have been applied in stripes or dots with gaps 30 between islands of nanoparticles 20, or in a layer with empty spaces or lakes 30 in a perforated layer of nanoparticles 20. The stripes, dots or perforated layer 20 are individually semicontinuous and permeable to liquid or vapor. Overall, layer 28 is discontinuous, and for a given layer thickness and nanoparticle diameter can have greater liquid or vapor permeability than layer 18 in FIG. 1 owing to the presence of the gaps, spaces or lakes 30.

Figure 3:
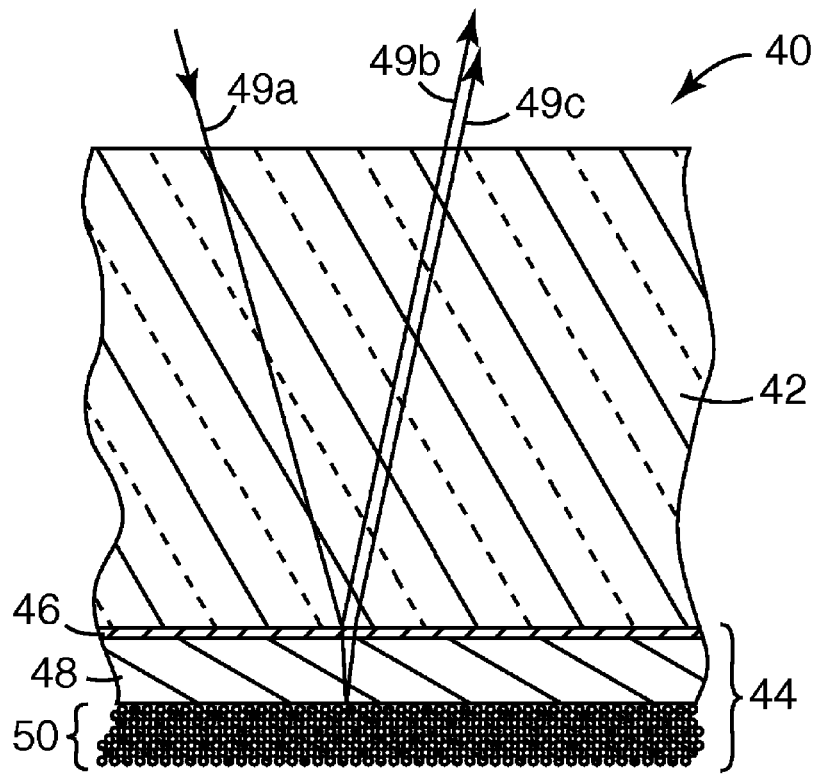
FIG. 3 is a schematic sectional view of a thin-film multilayer indicator that has a vapor-permeable reflective metal nanoparticle layer in accordance with the present invention.

FIG. 3 shows a schematic sectional view of an optically-responsive multilayer article 40. Article 40 includes a transparent substrate 42 and indicator 44. Indicator 44 includes continuous semireflective layer 46, porous detection layer 48 and semicontinuous liquid- or vapor-permeable reflective layer 50. Layer 50 contains metal nanoparticles 20 arranged in a morphology having sufficient thickness so that layer 50 has greater reflectivity than semireflective layer 46, while retaining sufficient porosity so that liquid or vapor can permeate through layer 50 to reach detection layer 48. A portion of ambient light represented by ray 49a passes through substrate 42, is reflected from semireflective layer 46 as light ray 49b, travels back through substrate 42, and then passes outside substrate 42. Another portion of ambient light ray 49a passes through substrate 42, semireflective layer 46 and detection layer 48 and is reflected from reflective layer 50 as light ray 49c. Light ray 49c travels back through detection layer 48, semireflective layer 46 and substrate 42, and then passes outside substrate 42. If an appropriate initial or changed thickness has been chosen for detection layer 48, and provided that layers 46 and 50 are sufficiently flat, then interference coloration will be created or destroyed within indicator 44 and light rays like rays 49b and 49c, and a visibly discernible change in the appearance of indicator 44 will be apparent when viewed through semireflective layer 46.

Figure 4:
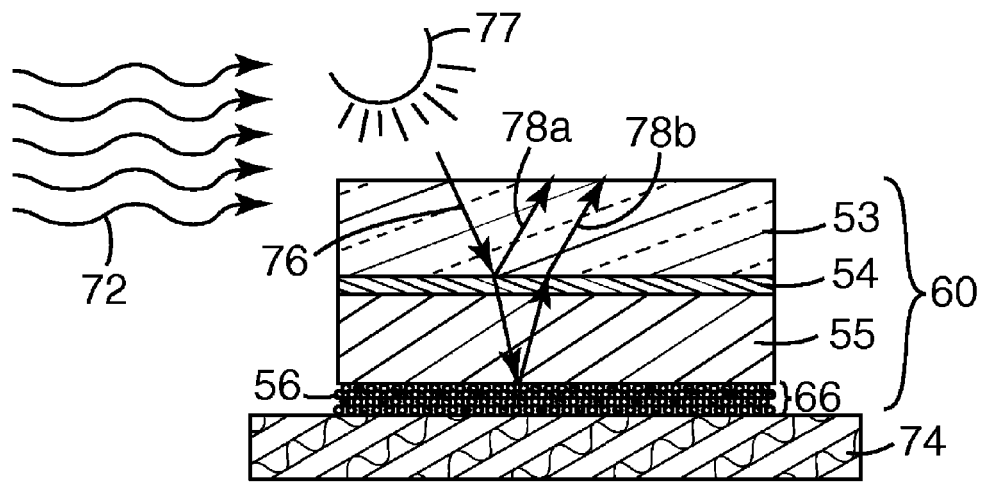
FIG. 4 through FIG. 6 are schematic side sectional views of a thin-film multilayer indicator that is mounted in proximity to various sorbent media.
Figure 5:
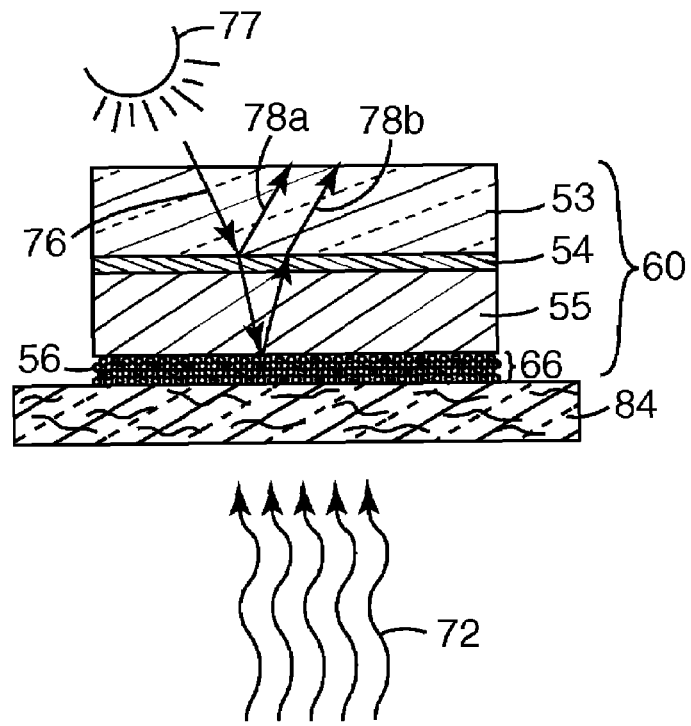
Figure 6:
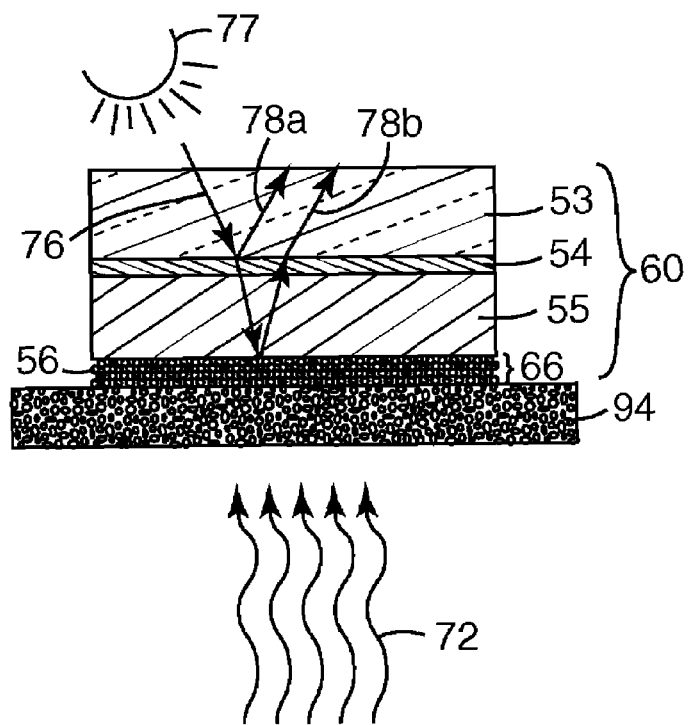

The disclosed device may be placed in proximity to a layer or body of sorbent media, or to both a layer of sorbent media and a body of sorbent media. FIG. 4 through FIG. 6 show schematic side sectional views of a various thin-film multilayer indicators in proximity to various layers of sorbent media. In FIG. 4, an organic vapor-containing air stream 72 flows across indicator 60 above glass substrate 53. A small piece of woven carbon paper 74 placed against vapor-permeable metal nanoparticle reflective layer 66 provides a path for organic vapors in air stream 72 to reach detection layer 55. Incident light rays such as ray 76 from light source 77 are reflected by semireflective layer 54 as first reflected ray 78*a* and by metal nanoparticle reflective layer 66 as second reflected ray 78*b*. FIG. 5 is similar to FIG. 4 but an organic vapor-containing air stream 72 reaches detection layer 55 through a piece of glass wool 84 placed against vapor-permeable metal nanoparticle reflective layer 66. FIG. 6 is similar to FIG. 4 and FIG. 5 but an organic vapor-containing air stream 72 reaches detection layer 55 through a piece of flexible microporous carbon-loaded nonwoven web 94 placed against vapor-permeable metal nanoparticle reflective layer 66.

A variety of metal nanoparticles may be employed in the disclosed optically-responsive multilayer reflective articles. Representative metals include silver, nickel, gold, platinum and palladium and alloys containing any of the foregoing. Metals prone to oxidation when in nanoparticle form (e.g., aluminum) might be used but desirably would be avoided in favor of less air-sensitive metals. The metal nanoparticles may be monolithic throughout or may have a layered structure (e.g., a core-shell structure such as an Ag/Pd structure). The nanoparticles may, for example, have an average particle diameter of about 1 to about 100, about 3 to about 50 or about 5 to about 30 nm. The overall thickness of the metal nanoparticle layer may, for example, be less than about 200 nm or less than about 100 nm, and the minimum layer thickness may, for example, be at least about 5 nm, at least about 10 nm or at least about 20 nm. Although large diameter microparticles might be applied to form a monolayer, the nanoparticle layer typically will be several nanoparticles thick, e.g., at least 2 or more, 3 or more, 4 or more or 5 or more nanoparticles, and with up to 5, up to 10, up to 20 or up to 50 nanoparticles total thickness. The metal nanoparticle reflective layer may, for example, have a reflectance of at least about 20%, at least about 40%, at least about 50% or at least about 60% at 500 nm.

Solutions or suspensions of suitable metal nanoparticles are available from several suppliers, including Inkjet Silver Conductor ink AG-IJ-G-100-S1 (from Cabot Printable Electronics and Displays); SILVERJET™ DGH 50 and DGP 50 ink (from Advanced Nano Products); SVW001, SVW102, SVE001, SVE102, NP1001, NP1020, NP1021, NP1050 and NP1051 inks from Nippon Paint (America); METALON™ FS-066 and JS-011 inks from Novacentrix Corp. and NP Series nanoparticle paste from Harima Chemicals, Inc. The metal nanoparticles may be borne in a variety of carriers, including water and organic solvents. The metal nanoparticles may also be borne in a polymerizable monomeric binder but desirably such binder is removed from the applied coating (using e.g., solvent extraction or sintering) so as to provide a permeable nanoparticle layer.

Several of the above-mentioned commercial metal nanoparticle products have been used as conductive paints or solder pastes for making circuit traces or joints. Typically the products are applied in their as-received form to a nonporous substrate, and form a conductive layer of ample thickness, e.g., 0.3 μm or more. The layer is sometimes sintered. Although permeability values are not typically provided by the suppliers, the traces or layers formed in such conductive paint and solder paste applications typically will individually be continuous within the trace or layer and impermeable to liquids and vapors.

The disclosed articles may be formed by applying a dilute coating solution or suspension of metal nanoparticles to an optically-responsive detection layer and allowing the solution or suspension to dry to form a semicontinuous liquid- or vapor-permeable light-reflective layer. The dilution level may, for example, be such as to provide a coating solution or suspension that will provide a suitably liquid- or vapor-permeable metal nanoparticle layer, for example solids levels less than 30 wt. %, less than 20 wt. %, less than 10 wt. %, less than 5% or less than 4%. By diluting an as-received commercial metal nanoparticle product with additional solvent and applying and drying the dilute solution or suspension, an appreciably thin, liquid- or vapor-permeable layer can be obtained. A variety of coating techniques can be employed to apply the metal nanoparticle solution or suspension, including swabbing, dip coating, roll coating, spin-coating, spray coating, die coating, ink jet coating, screen printing (e.g., rotary screen printing), gravure printing, flexographic printing and other techniques that will be familiar to persons having ordinary skill in the art. Spin-coating may provide a thinner, more permeable coating than is obtained using other methods. Accordingly, some silver nanoparticle suspensions available at low solids levels (such as 5 wt. % SVW001 silver from Nippon Paint or 10 wt. % SILVERJET DGH-50 or DGP-50 from Advanced Nano Products) might be usable in the as-received form without further dilution if spin-coated at an appropriately high speed and temperature onto a suitable substrate. The metal nanoparticle layer may be sintered after it has been applied (e.g., by heating at about 125 to about 250° C. for about 10 minutes to about 1 hour) so long as the sintering does not cause a loss of adequate permeability. It will be understood that the resulting reflective layer may no longer contain readily-identifiable nanoparticles, but that it may be referred to as a nanoparticle reflective layer to identify the manner in which it has been made.

Although liquid- or vapor-permeability may be provided by cracks, grain boundaries or other discontinuities in the metal nanoparticle layer, the desired permeability desirably is provided by forming a porous or microporous layer. The average pore size may, for example, be about 0.01 to about 1 μm, about 0.1 to about 0.5 μm or about 0.3 to about 100 nm. In general, larger pores are desired to impart liquid-permeability and smaller pores are needed to provide vapor-permeability. The nanoparticle layer may also or instead be patterned (for example, by applying impermeable metals) so as to create a pattern on exposure to an analyte. Selected surfaces of the nanoparticle layer may also or instead be covered or sealed off so that analyte only permeates in particular regions, again to provide a pattern on exposure.

A variety of optically-responsive detection layers may be employed in the disclosed articles. The surface of the detection layer upon which the metal nanoparticle layer is formed may be flat or may contain regular or irregular projections or depressions, e.g., light management features such as lenses and other structures that will be understood by persons having ordinary skill in the art. The embodiments shown in FIG. 1 through FIG. 6 provide a visibly discernible change in the appearance of the article (e.g., a change in color such as from green to red, an appearance or disappearance of color such as from white or black to colored or from colored to white or black, or a change from white to black or from black to white) to indicate the presence of the desired analyte. This represents a preferred embodiment that can provide a meaningful optical response without requiring external electronics, instrumentation or other components. A variety of detection layers may be employed, including not only those that provide such a visibly discernible appearance change but also others that may require external electronics, instrumentation or other components to indicate that the desired optical response has taken place. Suitable optical responses include changes in optical thickness, reflectivity, phase shift, polarization, birefringence, light transmission and other optical parameters that will be known to persons having ordinary skill in the art. Representative detection layers are disclosed, for example, in U.S. Pat. No. 4,778,987 (Saaski et al. '987), U.S. Pat. No. 4,945,230 (Saaski et al. '230), U.S. Pat. No. 5,611,998 (Aussenegg et al.), U.S. Pat. No. 5,783,836 (Liu et al.), U.S. Pat. No. 6,007,904 (Schwotzer et al.), U.S. Pat. No. 6,130,748 (Krüger et al.) and U.S. Pat. No. 6,590,665 B2 (Painchaud et al.); in Published PCT Application No. WO 2004/057314 A2 (Fiso Technologies Inc.); and in Published U.S. Patent Application Nos. US 2004/0062682 A1 (Rakow et al. '682) and US 2004/0184948 A1 (Rakow et al. '948), and in the above-mentioned U.S. patent application Ser. No. 11/530,614 filed even date herewith.

The detection layer may be homogeneous or heterogeneous, and may, for example, be made from a mixture of inorganic components, a mixture of organic components, or a mixture of inorganic and organic components. Detection layers made from a mixture of components may provide improved detection of groups of analytes. The detection layer may be porous or non-porous. The detection layer desirably is porous, especially when used in proximity to a layer or body of sorbent media. Porosity can be obtained by using porous materials such as foams made from high internal phase emulsions, such as those described in U.S. Pat. No. 6,573,305 B1 (Thunhorst et al.). Porosity may also be obtained via carbon dioxide foaming to create a microporous material (see "Macromolecules", 2001, vol. 34, pp. 8792-8801), or by nanophase separation of polymer blends (see "Science", 1999, vol. 283, p. 520). For detection layers that will provide a calorimetric indication of the presence of an analyte, the pore diameters preferably are smaller than the peak wavelength of the desired indicator coloration. For detection layers that will be used proximate a layer or body of sorbent media, the pores have a range of pore sizes or a surface area selected to provide liquid or vapor sorption characteristics like those of the sorbent media. Nano-sized pores are preferred for some applications, e.g., with average pore sizes of about 0.5 to about 20 nm, 0.5 to about 10 nm, or 0.5 to about 5 nm.

Representative inorganic detection layer materials include porous silica, metal oxides, metal nitrides, metal oxynitrides and other inorganic materials that can be formed into transparent (and if desired porous) layers of appropriate thickness for producing a suitable optical response such as a calorimetric change by optical interference. For example, the inorganic detection layer materials may be silicon oxides, silicon nitrides, silicon oxynitrides, aluminum oxides, titanium oxides, titanium nitride, titanium oxynitride, tin oxides, zirconium oxides, zeolites or combinations thereof. Porous silica is an especially desirable inorganic detection layer material due to its robustness.

Porous silicas may be prepared, for example, using a sol-gel processing route and made with or without an organic template. Exemplary organic templates include surfactants, e.g., anionic or nonionic surfactants such as alkyltrimethylammonium salts, poly(ethyleneoxide-co-propylene oxide) block copolymers and other surfactants or polymers that will be apparent to persons having ordinary skill in the art. The sol-gel mixture may be converted to a silicate and the organic template may be removed to leave a network of micropores within the silica. Representative porous silica materials are described in Ogawa et al., *Chem. Commun. pp.* 1149-1150 (1996), in Kresge et al., *Nature*, Vol. 359, pp. 710-712 (1992), in Jia et al., *Chemistry Letters*, Vol. 33(2), pp. 202-203 (2004) and in U.S. Pat. No. 5,858,457 (Brinker et al.). A variety of organic molecules may also be employed as organic templates. For example, sugars such as glucose and mannose may be used as organic templates to generate porous silicates, see Wei et al, *Adv. Mater.* 1998, Vol. 10, p. 313 (1998). Organo-substituted siloxanes or organo-bis-siloxanes may be included in the sol-gel composition to render the micropores more hydrophobic and limit sorption of water vapor. Plasma chemical vapor deposition may also be employed to generate porous inorganic detection materials. This methodology generally involves forming an analyte detection layer by forming a plasma from gaseous precursors, depositing the plasma on a substrate to form an amorphous random covalent network layer, and then heating the amorphous covalent network layer to form a microporous amorphous random covalent network layer. Examples of such materials are described in U.S. Pat. No. 6,312,793 (Grill et al.) and U.S. patent application Ser. No. 11/275,277 filed Dec. 21, 2005 and entitled PLASMA DEPOSITED MICROPOROUS ANALYTE DETECTION LAYER.

Representative organic detection layer materials include polymers, copolymers (including block copolymers) and mixtures thereof prepared or preparable from classes of monomers including hydrophobic acrylates and methacrylates, difunctional monomers, vinyl monomers, hydrocarbon monomers (olefins), silane monomers, fluorinated monomers, hydroxylated monomers, acrylamides, anhydrides, aldehyde-functionalized monomers, amine- or amine salt-functionalized monomers, acid-functionalized monomers, epoxide-functionalized monomers and mixtures or combinations thereof. The above-mentioned U.S. Patent Application Publication No. US 2004/0184948 A1 contains an extensive list of such monomers and reference is made thereto for further details. Polymers having intrinsic microporosity ("PIMs") provide particularly desirable detection layers. PIMs typically are non-network polymers that form microporous solids. Due to their typically highly rigid and contorted molecular structures, PIMs are unable to fill space efficiently, thus providing the disclosed microporous structure. Suitable PIMs include, but are not limited to, polymers disclosed in "Polymers of intrinsic microporosity (PIMs): robust, solution-processable, organic microporous materials," Budd et al., *Chem. Commun.*, 2004, pp. 230-231. Additional PIMs are disclosed in Budd et al., *J. Mater. Chem.*, 2005, 15, pp. 1977-1986, in McKeown et al., *Chem. Eur. J.* 2005, 11, No. 9, 2610-2620 and in Published PCT application No. WO 2005/012397 A2 (McKeown et al.).

One or more polymers within an organic detection layer may be at least partially crosslinked. Crosslinking may be desirable in some embodiments because it can increase mechanical stability and sensitivity to certain analytes. Crosslinking can be achieved by incorporating one or more multifunctional monomers into the detection layer, by subjecting the detection layer to, e.g., electron beam or gamma ray treatment, by adding or forming coordination compounds or ionic compounds in the detection layer, or by forming hydrogen bonds in the detection layer. In one exemplary embodiment, crosslinking is carried out in the presence of a porogen which may be subsequently extracted from the crosslinked system to yield a porous detection layer. Suitable porogens include, but are not limited to, inert organic molecules, such as normal alkanes (e.g., decane) or aromatics (e.g., benzene or toluene). Other crosslinked polymers include the above-mentioned highly crosslinked styrenic polymers.

If desired, the detection layer material may be treated to modify its surface properties or adsorption characteristics. A variety of such treatments may be employed, e.g., by exposing the micropores of an inorganic detection layer to a suitable organosilane compound. The detection layer may also or instead be treated with a suitable adhesion promoting material (e.g., a tie layer made of titanium or another suitable metal) to promote adhesion between an adjacent layer (e.g., a semireflective or reflective layer) and the detection layer.

For many applications, the detection layer desirably is hydrophobic. This will reduce the chance that water vapor (or liquid water) will cause a change in the detection layer optical response and interfere with the detection of an analyte, for example, the detection of organic solvent vapors.

The detection layer may be made from a single layer or from two or more sublayers. The sublayers may have a variety of configurations. For example, they may be stacked or arranged side by side. The sublayers may also be made from different materials selected to absorb different analytes. A layer or one of a set of sublayers may be discontinuous or patterned. The pattern may create or remove a colored image, word or message upon exposure to an analyte, thereby providing an easily identifiable warning for a user. Layer or sublayer patterns may also be formed by providing one or more portions that are reactive to a particular analyte and one or more portions that are non-reactive to the same analyte. A pattern of reactive material may also be deposited on a larger non-reactive sublayer, e.g., by making the patterned layer sufficiently thin so that no difference in optical thickness is apparent until an analyte is absorbed. The thickness of the detection layer may also be patterned, e.g., as described in U.S. Pat. No. 6,010,751 (Shaw et al.). This can permit a pattern to disappear (for example when a thinner portion swells to the same thickness as a thicker portion) or to appear (for example, when a portion shrinks to a lesser thickness than an adjacent portion).

The disclosed devices may be configured in a variety of relationships with respect to an analyte. For example, by configuring such a device in proximity to a suitable sorbent material so that it covers the full length of the liquid or vapor flow path through the material, an appearance change (e.g., a color change) "front" can advance with the flow of liquid or vapor through the sorbent material past the device. The advancing appearance change front could for example continuously indicate the remaining service life for the sorbent material (like a bar gauge or fuel gauge). The device could also be configured to give warning only at a desired remaining service life percentage. The device may if desired include a pattern or reference color to assist in visual discernment of changes in the appearance of the device. As mentioned, appearance changes in the device may be visibly monitored under ambient lighting. The device could be illuminated using an external light source such as a light emitting diode (LED) and evaluated using a photodetector to provide an optoelectronic signal. Whether viewed under ambient light or by using an external light source and photodetector, the breadth of analyte detection could if desired be increased in a variety of ways. For example, a small array of indicators traversing the liquid or vapor flow path could be employed. Each indicator could contain different detection layer materials (e.g., a silica detection layer, a detection layer applied by plasma-activated chemical vapor deposition ("PCVD"), and a detection layer made from PIMs. Also, a series of indicators could contain the same detection layer material (e.g., silica) treated using a series of different chemical treatments to provide a range of sorptive properties.

The disclosed devices may if desired be used in proximity to sorbent media capable of sorbing analytes expected to be present under the intended use conditions. The sorbent media desirably will be sufficiently porous to permit the ready flow of a liquid or vapor of interest therethrough, and may be in the form of a finely-divided solid (e.g., powder, beads, flakes, granules or agglomerates) or porous solid (e.g., an open-celled foam). Preferred sorbent media materials include activated carbon; alumina and other metal oxides that can remove a liquid or vapor of interest by adsorption; clay and other minerals treated with acidic solutions such as acetic acid or alkaline solutions such as aqueous sodium hydroxide; molecular sieves and other zeolites; other inorganic sorbents such as silica; and organic sorbents including hyper-crosslinked systems, such as the highly crosslinked styrenic polymers known as "Styrosorbs" (as described for example in V. A. Davankov and P. Tsyurupa, Pure and *Appl. Chem., vol.* 61, pp. 1881-89 (1989) and in L. D. Belyakova, T. I. Schevchenko, V. A. Davankov and M. P. Tsyurupa, *Adv. in Colloid and Interface Sci.* vol. 25, pp. 249-66, (1986)). Activated carbon and alumina are particularly preferred sorbent media. Mixtures of sorbent media can be employed, e.g., to absorb mixtures of liquids or vapors of interest. If in a finely divided form, the sorbent particle size can vary a great deal and usually will be chosen based in part on the intended service conditions. As a general guide, finely-divided sorbent media particles may vary in size from about 4 to about 3000 micrometers average diameter, e.g., from about 30 to about 1500 micrometers average diameter. Mixtures of sorbent media particles having different size ranges can also be employed, (e.g., in a bimodal mixture of sorbent media particles or in a multilayer arrangement employing larger sorbent particles in an upstream layer and smaller sorbent particles in a downstream layer). Sorbent media combined with a suitable binder (e.g., bonded carbon) or captured on or in a suitable support such as described in U.S. Pat. No. 3,971,373 (Braun et al.), U.S. Pat. No. 4,208,194 (Nelson) and U.S. Pat. No. 4,948,639 (Brooker et al.) and in U.S. Patent Application Publication No. US 2006/0096911 A1 (Brey et al.) may also be employed.

The disclosed devices may be rigid or flexible. Flexible devices desirably are sufficiently bendable without fracturing so that they can be made using one or more roll processing steps, and if need be bent in use, e.g., around the inside of a cartridge or other enclosure. The device may be attached to a support or other component using a variety of techniques, including film or bulk adhesives, mechanical inserts, thermal bonding, ultrasonic welding and combinations thereof.

A substrate is optional, but when present it may be made from a variety of materials capable of providing a suitably transparent support for the disclosed device. The substrate may be rigid (e.g., glass) or flexible (e.g., a plastic film that may be handled in one or more roll processing steps). If made of a flexible material such as a suitably transparent plastic, the substrate may desirably have sufficiently low liquid- or vapor-permeability so that the liquid(s) or vapor(s) of interest will not be transmitted into or out of the disclosed device through the substrate. A porous substrate may, for example, be placed between the disclosed device and a layer or body of sorbent media.

Some of the disclosed devices include both semireflective and reflective layers. One or both of the semireflective and reflective layers may be made using a solution or suspension of metal nanoparticles. The semireflective or reflective layers may each be made from a variety of other materials that provide diffuse or preferably specular light reflection and if need be can cooperate when appropriately spaced apart to provide a readily visibly perceptible indicator appearance change. Suitable semireflective and reflective layer materials include metals such as aluminum, chromium, gold, nickel, silicon, silver, palladium, platinum, titanium and alloys containing such metals; metal oxides such as chrome oxide, titanium oxide and aluminum oxide; and the multilayer optical films (including birefringent multilayer optical films) described in U.S. Pat. No. 5,699,188 (Gilbert et al.), U.S. Pat. No. 5,882,774 (Jonza et al.) and U.S. Pat. No. 6,049,419 (Wheatley et al.), and PCT Published Application No. WO 97/01778 (Ouderkirk et al.). The semireflective and reflective layers may be the same or different. If desired, discontinuities may be formed in one or both of the semireflective or reflective layers in the pattern of a shape, letter, symbol, or message. This can cause a discernible pattern to emerge or disappear upon exposure to the vapor(s) of interest. A viewer may find it easier to discern the contrasting color of such a pattern than to discern a calorimetric change in the overall device. When used, the semireflective layer is less reflective than the reflective layer and transmits some incident light. The semireflective layer may, for example, have a physical thickness of about 2 to about 50 nm, light transmission at 500 nm of about 20 to about 80%, and reflectance at 500 nm of about 80 to about 20%. The reflective layer may, for example, have a physical thickness of about 1 to about 500 nm, light transmission at 500 nm of about 0 to about 80%, and reflectance at 500 nm of about 100 to about 20%. The faces of paired semireflective and reflective layers desirably are flat to within about ±10 nm.

The disclosed devices may include additional layers or elements if desired. For example, a porous layer of sorbent-loaded composite (e.g., a web of activated carbon particles ensconced in a matrix of fibrillated PTFE such as is described in the above-mentioned U.S. Pat. No. 4,208,194) may be placed between a semireflective or reflective layer and a layer or body of sorbent media, to homogenize vapors permeating into the device or otherwise moderate the optical response to conditions in the sorbent media.

The disclosed devices may be used for a variety of applications including chemical or biological sensors, organic vapor respirators, powered air purifying respirators (PAPRs), hazmat suits, collective protection filters and other applications that will be familiar to persons having ordinary skill in the art.

The invention is further illustrated in the following illustrative examples, in which all parts and percentages are by weight unless otherwise indicated. The abbreviations shown below in Table 1 were employed in some of the examples:

TABLE 1

| ABBREVIATION | DESCRIPTION |
|---|---|
| BC | bis-catechol; 5,5',6,6'-tetrahydroxy-3,3,3',3'-tetramethyl-1,1'-spirobisindane |
| FA | fluorinated arene; tetrafluoroterephthalonitrile |
| DMF | N,N-dimethylformamide |
| THF | Tetrahydrofuran |

EXAMPLE 1

A thin film indicator was prepared using polymers of intrinsic microporosity (PIMs) as the detection layer, an Au/Pd semireflective layer, and a silver nanoparticle vapor-permeable reflective layer. PIM polymer was prepared from the monomers BC and FA generally according to the procedure reported by Budd et al. in *Advanced Materials,* 2004, Vol. 16, No. 5, pp. 456-459. 9.0 grams of BC were combined with 5.28 g of FA, 18.0 g potassium carbonate, and 120 milliliters of DMF and the mixture was reacted at 70° C. for 24 hours. The resulting polymer was dissolved in THF, precipitated three times from methanol, and then dried under vacuum at room temperature. A yellow solid product was obtained having a molecular weight (Mw) of 61,800.

A glass slide was sputter coated with a 5 nm thick layer of Au/Pd, using a DENTON™ Vacuum Desk II sputter coater from Denton Vacuum equipped with an Au/Pd target with a 60:40 Au:Pd mass ratio. The sputter coating power and coating duration were 35 milliamps and 20 seconds respectively, under a vacuum of 100 millitorr. The PIM polymer was then spin-coated onto the Au/Pd layer using a 4% solution of the above-described PIM polymer in chlorobenzene coated onto the Au/Pd layer at 750 rpm. Next, two different indicators were prepared by applying a silver nanoparticle suspension to the PIM polymer layer. Indicator A was prepared using NPS-J silver nanoparticle suspension (60% in tetradecane) from Harima Corporation. Transmission Electron Microscopy (TEM) analysis of the particles revealed a size distribution of approximately 2 to 10 nm in diameter. A 0.08 g quantity of the as-received nanoparticle suspension was mixed with 2 milliliters of heptane to provide a diluted suspension containing about 3.3% silver. The diluted suspension was spin-coated onto the PIM film at 500 rpm to provide a vapor-permeable reflective layer having a reflectivity of about 62% at 500 nm relative to a 100 nm thick aluminum reference layer. Indicator B was prepared using SVE 102 silver nanoparticle suspension (30% in ethanol, 30 nm mean particle diameter) from Nippon Paint (America) Corporation. A 0.7 g quantity of this as-received suspension was mixed with 2 milliliters of ethanol to provide a diluted suspension containing about 9.1% silver. The diluted suspension was spin-coated onto the PIM film at 1000 rpm to provide a vapor-permeable nanoparticle reflective layer having a reflectivity of about 70% at 500 nm relative to a 100 nm thick aluminum reference layer.

Figure 7:
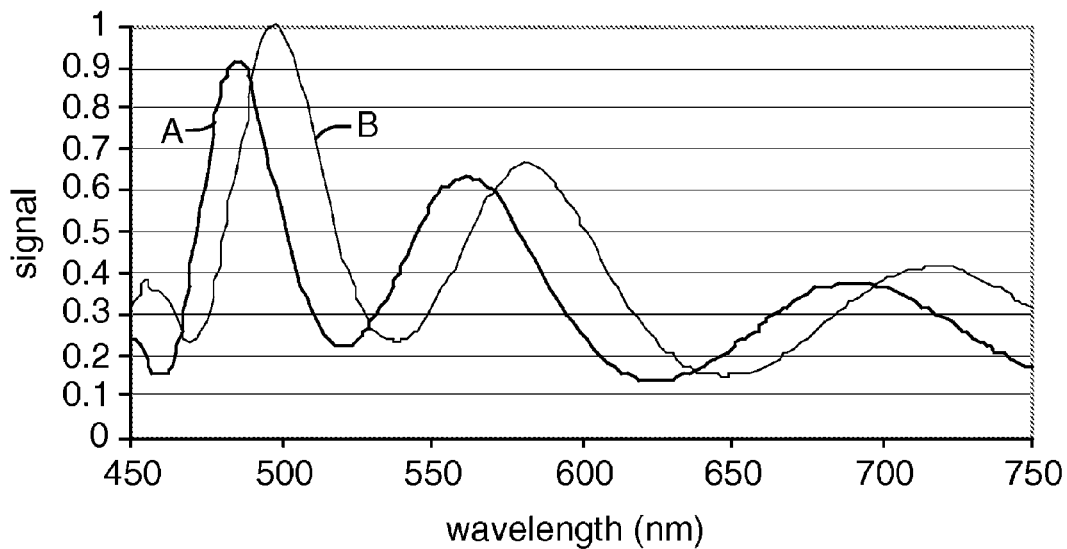
FIG. 7 through FIG. 9 are plots showing the response of various thin-film multilayer indicators to a toluene challenge.
Figure 8:
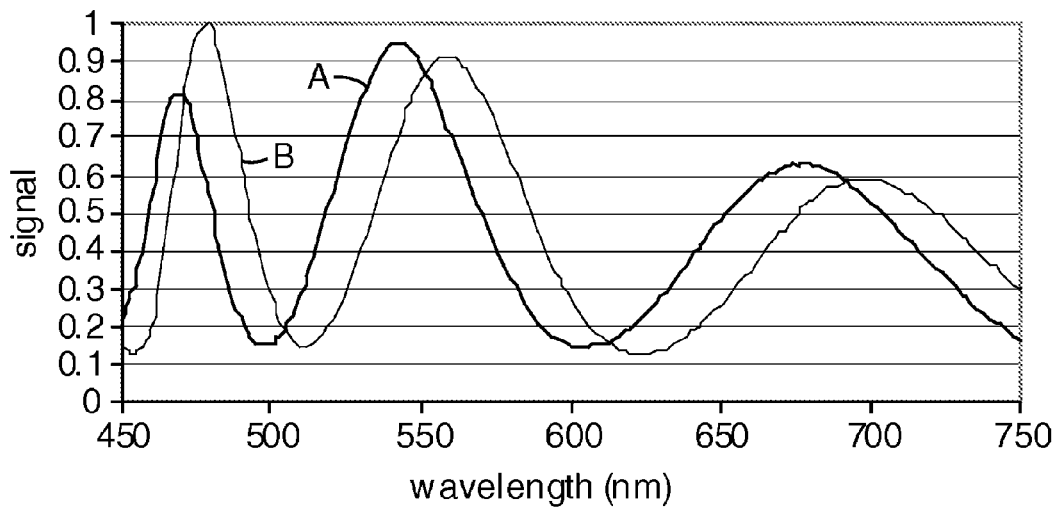

To assess the ability of the resulting thin film indicators to compete with microporous carbon for adsorption of organic vapors, the indicators were placed upon a small piece of carbon-loaded blown microfiber (BMF) nonwoven web, with the vapor-permeable nanoparticle reflective layer in contact with the web and its microporous carbon. The carbon-loaded BMF web contained 40×140 mesh activated carbon granules derived from coconut shells (from Pacific Activated Carbon Co.), dispersed throughout an elastic fibrous web made from IROGRAN™ PS 440-200 thermoplastic polyurethane (from Huntsman International LLC), prepared as described in U.S. Patent Application Publication No. US 2006/0096911 A1 (Brey et al.). The fibrous web had a 17 micrometer effective fiber diameter and a 500 g/m$^2$ carbon loading level, corresponding to about a 0.22 g/cm$^3$ carbon density. When at equilibrium with 1000 ppm of cyclohexane flowing at 32 liters/min, the carbon in this nonwoven web layer adsorbs about 0.21 g cyclohexane per g carbon. The indicators were illuminated and observed through the glass substrate using a spectrometer and fiber optic reflection probe while toluene vapor passed through the carbon-loaded layer and past the indicator. In FIG. 7, Curve A and Curve B respectively represent the initial signal and the signal at 50 ppm toluene for indicator A. Similarly, in FIG. 8, Curve A and Curve B respectively represent the initial signal and the signal at 50 ppm toluene for indicator B. Indicator A exhibited a peak signal wavelength shift of about 20 nm (from about 564 nm to about 584 nm) when challenged with 50 ppm toluene. Indicator B exhibited a peak signal wavelength shift of about 17 nm (from about 544 nm to about 561 nm) when challenged with 50 ppm toluene. Indicators A and B both maintained their sorptive functionality when placed in thermodynamic competition with microporous carbon.

EXAMPLE 2

Figure 9:
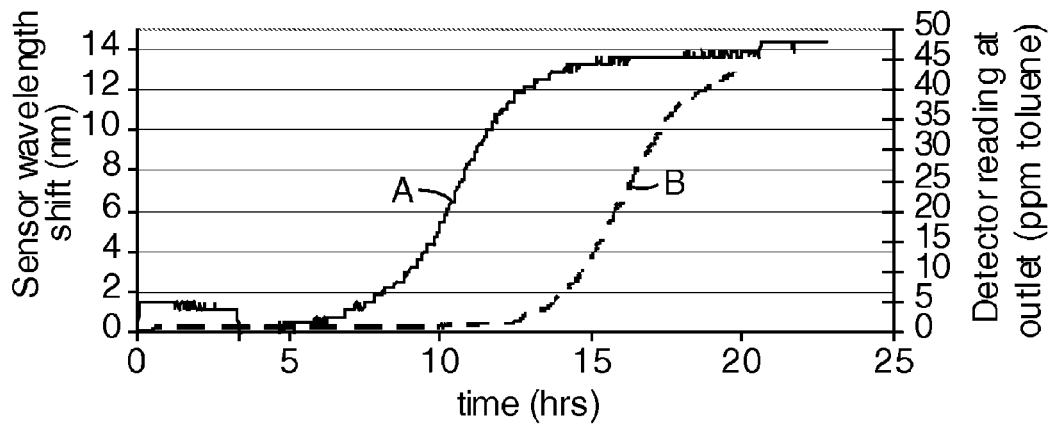

Using the method of Example 1, 1 mm thick glass slides were sputter coated with a 5 nm thick layer of Au/Pd, followed by spin-coating (at 1500 rpm) a layer of PIM polymer onto the Au/Pd layer. Using the method of Example 1 (Indicator B), a diluted SVE 102 silver nanoparticle suspension was spin-coated onto the PIM film to provide a vapor-permeable nanoparticle reflective layer. The resulting thin-film indicator had a green-yellow appearance when visually observed through the glass slide. DYMAX™ No. OP-4-20641A UV-cure optical adhesive from Dymax Corporation was used to adhere the indicator to the inside sidewall of a filtration cartridge made from clear polycarbonate resin, with the vapor-permeable nanoparticle reflective layer facing the cartridge interior. The cartridge was filled with 45.7 g of activated carbon sorbent. Several small holes were drilled in the cartridge cover immediately above and upstream from the indicator to ensure adequate vapor flow at the indicator/sorbent bed interface. The cartridge was challenged using 50 ppm toluene in dry air (<3% RH) flowing at 64 liters/min. The indicator was monitored through the polycarbonate cartridge body at 50-60% of the bed depth using a fiber optic reflection probe having a <1 mm illumination spot diameter and an Ocean Optics spectrometer. Between 6 and 16 hours after the start of the toluene challenge, the indicator exhibited a gradual red-shift in coloration amounting to 14 nm in total. Taking into account the indicator's position in the cartridge, the timing and magnitude of the indicator response were consistent with separately-collected concentration data obtained using a MULTIRAE™ IR photo-ionization detector from RAE Systems Inc. positioned at the cartridge outlet. The indicator data and IR photo-ionization detector data are plotted in FIG. 9.

Figure 10:
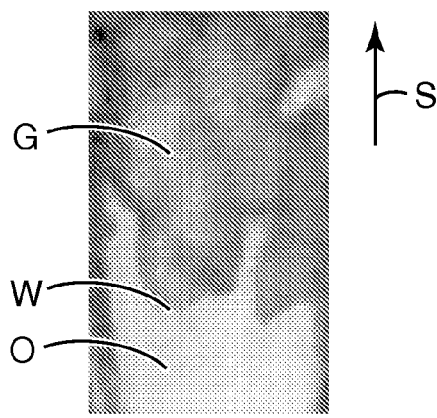
FIG. 10 and FIG. 11 are black-and-white renderings of colored wavefronts moving across thin-film multilayer indicators.

A second cartridge was assembled in the same fashion and challenged with 500 ppm styrene in dry air (<3% RH) flowing at 64 liters/min. A QX5™ computer microscope from Digital Blue Corporation was angularly adjusted so that the indicator initially appeared green when observed, and used to record the indicator's appearance when challenged with styrene vapor. As the challenge progressed, the indicator's initial green coloration changed to orange along a color change front that moved from the cartridge inlet towards its outlet. An RGB histogram of the initial green coloration returned mean values of r=145, g=191, and b=121. After the indicator responded to the styrene vapor by changing from green to orange, the histogram values were r=208, g=179, and b=127. FIG. 10 shows a black and white rendering of the indicator coloration part-way through the experiment and illustrates the vapor wavefront progression and appearance. The green and orange visible portions are identified with the letters G and O, the wavefront is identified with the letter W and the styrene flow direction is identified with the letter S.

EXAMPLE 3

Figure 11:

Using the method of Example 1, PIM polymer was prepared from the monomers BC and FA. Using a CHA Industries Mark-50 evaporator operated at a base pressure of $1 \times 10^{-5}$ torr and No. T-2003 titanium pellets (99.995% purity, 6×6 mm, from Cerac Inc.), cleaned glass slides were metallized with a 10 nm thick semireflective Ti layer. A 4% solution of the PIM polymer in chlorobenzene was spin-coated onto the Ti layer at 1000 rpm. Using the method of Example 1 (Indicator B), a diluted SVE 102 silver nanoparticle suspension was spin-coated onto the PIM film to provide a vapor-permeable reflective layer. Following silver nanoparticle deposition, the film sample was heated at 150° C. in air for 1 hour. The resulting thin-film indicator had a green appearance when visually observed through the glass slide. DYMAX™ No. OP-4-20641A UV-cure optical adhesive was used to adhere the indicator to an additional glass slide layer. The resulting glass slide stack was adhered to the inner sidewall of a filtration cartridge made from clear polycarbonate plastic. Next, using a method like that described in U.S. Pat. No. 4,153,661 (Ree et al.) and Example 1 of U.S. Pat. No. 4,208,194, a dough was formed by combining an aqueous polytetrafluoroethylene ("PTFE") particle dispersion with finely ground, activated carbon particles. The dough was milled and dried but not calendared to provide a composite web of activated carbon particles ensconced in a matrix of fibrillated PTFE. A layer of the carbon composite web was attached to the top edge of the glass slide stack and folded down to cover the porous nanoparticle reflective layer. The remaining filtration cartridge volume was then filled with 45.8 g of activated carbon sorbent. Several small holes were drilled in the cartridge cover immediately above and upstream from the indicator to ensure adequate vapor flow at the indicator/sorbent bed interface. The cartridge was challenged with 200 ppm styrene in dry air (<3% RH) at a 32 liters/min flowrate. Using ambient lighting, a TRENDnet™ Model TV-IP201W wireless camera (from TRENDnet Company) was angularly adjusted so that the indicator initially appeared green when observed, and used to record the indicator's appearance when challenged with styrene vapor. As the experiment progressed, the indicator color changed from the initial green color to deep red, with the color change appearing first near the filtration cartridge inlet and moving towards the cartridge outlet. When the vapor flow was stopped, the wavefront blurred slightly but did not move closer to or farther from the cartridge outlet. An RGB histogram of the initial green color returned mean values of r=30, g=99, and b=51. After the indicator responded to the styrene vapor by changing green to red, the histogram values were r=97, g=56, and b=66. FIG. 11 shows a black and white rendering of the indicator coloration part-way through the experiment and illustrates the vapor wavefront progression and appearance. The carbon sorbent is identified with the letter C, the green and red visible indicator portions are identified with the letters G and R, the wavefront is identified with the letter W and the styrene flow direction is identified with the letter S. The wavefront was noticeably more uniform than the wavefront in FIG. 10, which involved a filtration cartridge that did not include a carbon composite web between the indicator and the sorbent media.

EXAMPLE 4

Using the method of Example 3, a 10 nm thick titanium semireflective layer was evaporatively coated onto a cleaned glass slide. The Ti-coated glass slide was next mounted onto a planar electrode. The electrode was in turn mounted in an aluminum vacuum chamber equipped with turbomolecular pump in series with a Roots blower and a dry mechanical pump. The chamber was closed and pumped down to a base pressure of 0.0005 Torr. A mixture of tetramethylsilane, oxygen and butadiene gases was introduced into the chamber at respective flow rates of 100 standard cubic centimeters per minute (sccm), 100 sccm and 160 sccm. A plasma was formed by powering the planar electrode using a Model RF50S radio frequency power supply (from RF Power Products) operating through a Model AMN3000 impedance matching network (from PlasmaTherm Inc.). While the plasma was in operation the delivered power was maintained at 75 watts and the chamber pressure was maintained at 37 mTorr. Deposition was carried out for 14 minutes to yield a plasma-deposited thin organic film having a 0.768 micrometer thickness. The plasma-deposited thin film was annealed in a vacuum furnace at a temperature of 450° C. for 1 hour to provide a microporous thin film detection layer atop the titanium semireflective layer. A 0.0475 g quantity of SILVER NANOINK™ silver nanoparticle slurry in methanol (Lot S Ag 031027W, from Advanced Nano Products Co., Ltd, Korea) was diluted with an additional 2 milliliters of methanol to provide a dilute suspension which was spin-coated onto the thin film detection layer at 1500 rpm. The resulting spin-coated silver nanoparticle layer was allowed to dry, yielding a vapor-permeable thin film silver nanoparticle reflective layer atop the thin film detection layer.

Figure 12:
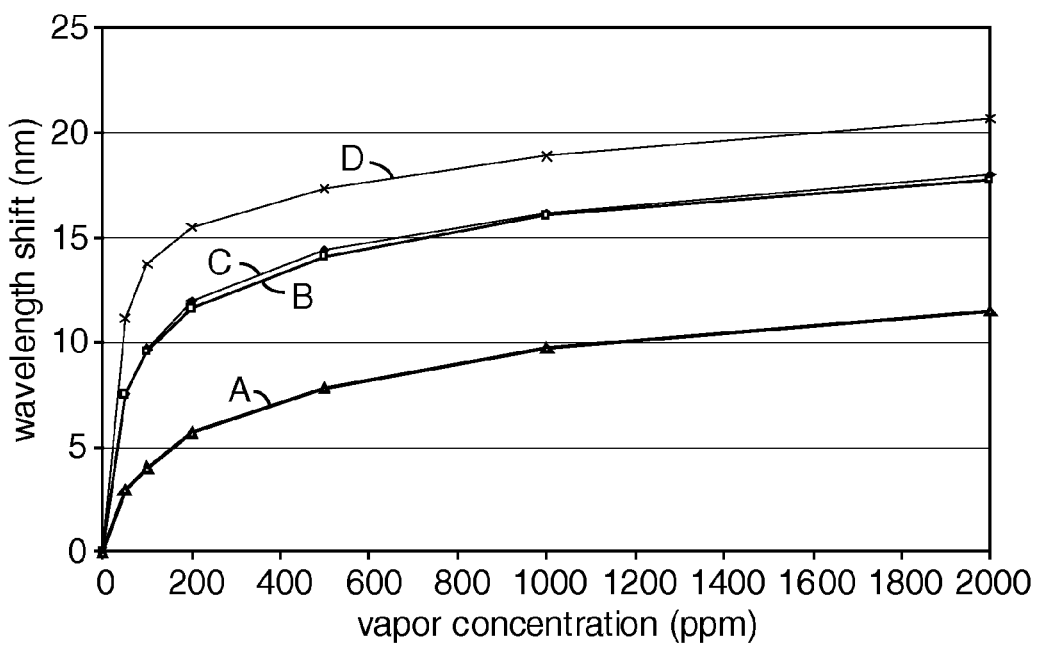
FIG. 12 is a plot showing the response of a thin-film multilayer indicator to challenges from several vapors.

To assess the ability of the resulting indicator to compete with microporous carbon for adsorption of organic vapors, the indicator was placed upon a small piece of the carbon composite web employed in Example 3, with the permeable nanoparticle reflective layer in contact with the carbon composite web. The indicator appearance was observed through the glass substrate using a spectrometer and fiber optic reflection probe to evaluate the sensor coloration. The sensor was exposed to toluene, methyl ethyl ketone and ethylbenzene vapor streams passing through the carbon composite web. The toluene and methyl ethyl ketone streams were maintained at less than 5% relative humidity and the ethylbenzene stream was maintained at 82% relative humidity. The results are shown in FIG. 12, where Curves A, C and D respectively show the methyl ethyl ketone, toluene and ethylbenzene vapor concentration vs. the observed wavelength shift, and where Curve B shows the toluene vapor concentration vs. the observed wavelength shift when the carbon composite web was not employed. The results in FIG. 12 show that the disclosed indicator exhibited significant wavelength shifts for all vapors. Curves B and C show that the disclosed indicator exhibited wavelength shifts of about 6 to 16 nm at a 200 ppm vapor concentration, and wavelength shifts of about 12 to 21 nm at a 2000 ppm vapor concentration. Curves B and C also show that the porous detection layer in the disclosed indicator maintained its sorptive capability even when placed in thermodynamic competition with microporous carbon.

EXAMPLE 5

Using the method of Example 1, PIM polymer was prepared from the monomers BC and FA. Using a CHA Industries Mark-50 evaporator operated at a base pressure of $1 \times 10^{-5}$ torr and No. T-2003 titanium pellets, cleaned glass slides were metallized with a 10 nm thick semireflective layer of Ti. A 4% solution of the PIM polymer in chlorobenzene was spin-coated onto the Ti layer at 2000 rpm. Using the method of Example 1 (Indicator B), a diluted SVE 102 silver nanoparticle suspension was spin-coated onto the PIM film and dried under vacuum at room temperature for 12 hours to provide a multilayer thin-film indicator with a PIM detection layer located between a titanium semireflective layer and a vapor-permeable metal nanoparticle reflective layer. The indicator had a green appearance when visually observed through the glass slide and semireflective layer.

To assess the ability of the indicator to compete with microporous carbon for adsorption of organic vapors, the indicator was placed upon a small piece of carbon-loaded nonwoven web containing about 500 g/m² (corresponding to an effective carbon density of about 0.22 g/cc) of 40×140 mesh activated carbon granules derived from coconut shells (from Pacific Activated Carbon Co.), dispersed throughout an elastic fibrous web made from IROGRAN™ PS 440-200 thermoplastic polyurethane (from Huntsman International LLC), prepared as described in U.S. Patent Application Publication No. US 2006/0096911 A1 (Brey et al.). At equilibrium with 1000 ppm of cyclohexane flowing at 32 liters/min, the carbon in the layer adsorbs 0.21 g cyclohexane per gram of carbon. The indicator appearance was observed through the glass substrate using a spectrometer and fiber optic reflection probe, and measured in dry air (<3% RH) and at 85% relative humidity. The indicator exhibited only a 3 nm spectral shift at 85% relative humidity compared to the results in dry air, thus demonstrating that the indicator was generally insensitive to high humidity conditions. Next, while maintaining an 85% relative humidity atmosphere, the carbon-loaded nonwoven web was exposed to styrene vapor at 20 ppm. The indicator exhibited a 23 nm spectral shift, demonstrating that the indicator maintained its sorptive functionality when placed in thermodynamic competition with microporous carbon exposed to a humid analyte stream.

EXAMPLE 6

Using the method of Example 5, a 10 nm thick titanium semireflective layer was evaporatively coated onto two cleaned glass slides. PIM polymer with a weight average molecular weight (Mw) of 62,900 was prepared using the method of Example 1 and the monomers BC and FA. A 3.2% solution of the PIM polymer in a 60/40 chlorobenzene/tetrahydropyran mixture was spin-coated onto the Ti layers of the coated glass slides at 1000 rpm. A 1.0 g quantity of SILVERJET™ DGP 40LT-25C silver nanoparticles (43.25% in methanol, from Advanced Nano Products Co., Ltd., Korea) was added to 2 milliliters methanol to give a diluted suspension containing 16.8% solids. The diluted suspension was spincoated at 600 rpm onto the PIM layer on each coated slide. One slide was then air dried and identified as indicator A. The other slide was heated at 150° C. for 1 hour in air to partially sinter the silver particles and identified as indicator B. Indicator B had a reflectivity of about 39% at 500 nm relative to a 100 nm thick aluminum reference layer.

To assess the abilities of both indicators to compete with microporous carbon for adsorption of organic vapors, the coated side of each slide was placed against a small piece of the carbon-loaded web 94 used in Example 2, with the permeable nanoparticle reflector in contact with the carbon-loaded web. The indicators were observed through the glass substrate and semireflective layer using a spectrometer and fiber optic reflection probe. The indicators were exposed to a 50 ppm toluene vapor stream passing through the carbon-loaded web. The spectral peak for Indicator A shifted from 532 nm to 558 nm, and the spectral minimum for Indicator B shifted from 609 nm to 629 nm, demonstrating that in each instance the indicator maintained sorptive functionality when placed in thermodynamic competition with microporous carbon.

All patents and patent applications cited above, including those in the Background section, are incorporated by reference into this document in total. To the extent that there is a conflict, this document will prevail.

A number of embodiments of the invention have been described. Nevertheless, it will be understood that various modifications may be made without departing from the invention. Accordingly, other embodiments are within the scope of the following claims.

We claim:

1. A method for forming an optically-responsive multilayer reflective article, which method comprises applying a dilute solution or suspension of metallic nanoparticles to an optically-responsive detection layer and allowing the solution or suspension to dry to form a semicontinuous liquid- or vapor-permeable light-reflective layer that has the nanoparticles contacting each other in a stacked arrangement and that will permit a liquid or vapor analyte to pass through the light-reflective layer to cause an optically-responsive change in the detection layer in the presence of the analyte.

2. A method according to claim 1 wherein the dilute solution or suspension has a solids level less than 30%.

3. A method according to claim 1 wherein the dilute solution or suspension has a solids level less than 10%.

4. A method according to claim 1 wherein the dilute solution or suspension has a solids level less than 5%.

5. A method according to claim 1 wherein the nanoparticles comprise silver or an alloy containing silver.

6. A method according to claim 1 wherein the nanoparticles comprise nickel, gold, platinum, palladium or an alloy containing any of the foregoing.

7. A method according to claim 1 wherein the nanoparticles have an average particle diameter of about 3 to about 50 nm.

8. A method according to claim 1 wherein the light-reflective layer has a thickness less than about 200 nm.

9. A method according to claim 1 wherein the light-reflective layer has a thickness less than about 100 nm.

10. A method according to claim 1 wherein the light-reflective layer is discontinuous.

11. A method according to claim 1 wherein the light-reflective layer has a reflectance of at least about 20% at 500 nm.

12. A method according to claim 1 wherein the light-reflective layer has a reflectance of at least about 50% at 500 nm.

13. A method according to claim 1 further comprising sintering the light-reflective layer.

14. A method according to claim 1 wherein the detection layer is porous.

15. A method according to claim 14 wherein the detection layer comprises porous silica.

16. A method according to claim 1 further comprising forming the detection layer by plasma-activated chemical vapor deposition.

17. A method according to claim 1 wherein the detection layer comprises a polymer of intrinsic microporosity.

18. A method according to claim 17 wherein the detection layer comprises a polymer of bis-catechol and a fluorinated arene.

19. A method according to claim 1 wherein the detection layer exhibits a change in optical thickness in the presence of an analyte.

20. A method according to claim 1 wherein the detection layer exhibits a change in light phase shift, polarization, birefringence or transmission in the presence of an analyte.

21. An optically-responsive multilayer reflective article that comprises an optically-responsive detection layer in fluid communication with a semicontinuous liquid- or vapor-permeable light-reflective metal nanoparticle layer that has the nanoparticles contacting each other in a stacked arrangement and that will permit a liquid or vapor analyte to pass through the light-reflective layer and cause an optically-responsive change in the detection layer in the presence of the analyte.

22. An article according to claim 21 wherein the nanoparticles comprise silver or an alloy containing silver.

23. An article according to claim 21 wherein the nanoparticles comprise nickel, gold, platinum, palladium or an alloy containing any of the foregoing.

24. An article according to claim 21 wherein the nanoparticles have an average particle diameter of about 3 to about 50 nm.

25. An article according to claim 21 wherein the light-reflective layer has a thickness less than about 200 nm.

26. An article according to claim 21 wherein the light-reflective layer has a thickness less than about 100 nm.

27. An article according to claim 21 wherein the light-reflective layer is discontinuous.

28. An article according to claim 21 wherein the light-reflective layer has a reflectance of at least about 20% at 500 nm.

29. An article according to claim 21 wherein the light-reflective layer has a reflectance of at least about 50% at 500 nm.

30. An article according to claim 21 wherein the light-reflective layer is sintered.

31. An article according to claim 21 wherein the detection layer is porous.

32. An article according to claim 31 wherein the detection layer comprises porous silica.

33. An article according to claim 31 wherein the detection layer comprises a polymer of intrinsic microporosity.

34. An article according to claim 33 wherein the detection layer comprises a polymer of bis-catechol and a fluorinated arene.

35. An article according to claim 21 wherein the detection layer has been formed by plasma-activated chemical vapor deposition.

36. An article according to claim 21 wherein the detection layer exhibits a change in optical thickness in the presence of an analyte.

37. An article according to claim 21 wherein the detection layer exhibits a change in light phase shift, polarization, birefringence or transmission in the presence of an analyte.

38. An indicator comprising a layer or bed of sorbent media proximate an article according to claim 21.

39. An indicator according to claim 38 further comprising a porous layer of sorbent-loaded composite between the article and a bed of sorbent media.

* * * * *

UNITED STATES PATENT AND TRADEMARK OFFICE
CERTIFICATE OF CORRECTION

| | | |
|---|---|---|
| PATENT NO. | : 7,906,223 B2 | Page 1 of 1 |
| APPLICATION NO. | : 11/530619 | |
| DATED | : March 15, 2011 | |
| INVENTOR(S) | : Neal A Rakow et al. | |

It is certified that error appears in the above-identified patent and that said Letters Patent is hereby corrected as shown below:

Column 1
Line 19, delete "calorimetric" and insert -- colorimetric --, therefor.

Column 2
Line 53, delete "detectable" and insert -- detectible --, therefor.

Column 7
Line 32, delete "calorimetric" and insert -- colorimetric --, therefor.

Column 11
Line 13, delete "calorimetric" and insert -- colorimetric --, therefor.

Signed and Sealed this
Seventeenth Day of May, 2011

David J. Kappos
*Director of the United States Patent and Trademark Office*